United States Patent
Okuda et al.

[11] Patent Number: 5,910,187
[45] Date of Patent: Jun. 8, 1999

[54] METHOD OF DETECTING YARN UNEVENNESS

[75] Inventors: Kazuhiko Okuda; Hideki Oohata, both of Amagasaki, Japan

[73] Assignee: Keisokki Kogyo Co., Ltd., Amagasaki, Japan

[21] Appl. No.: 08/866,221

[22] Filed: May 30, 1997

[30] Foreign Application Priority Data

Jul. 2, 1996 [JP] Japan ................................. 8-192876

[51] Int. Cl.$^6$ ................................................ G01N 27/00
[52] U.S. Cl. ................................................ 73/160; 73/159
[58] Field of Search ........................... 73/160, 159, 158

[56] References Cited

U.S. PATENT DOCUMENTS

| | | | |
|---|---|---|---|
| 3,831,444 | 8/1974 | Sasaki et al. | 73/160 |
| 3,945,181 | 3/1976 | Yamazaki et al. | 73/160 |
| 4,491,831 | 1/1985 | Sakai et al. | 340/677 |
| 4,774,673 | 9/1988 | Aemmer | 73/160 |
| 5,570,188 | 10/1996 | Nevel et al. | 356/385 |
| 5,592,849 | 1/1997 | Nakade et al. | 73/160 |

*Primary Examiner*—Max H. Noori
*Attorney, Agent, or Firm*—Sixbey, Friedman, Leedom & Ferguson; David S. Safran

[57] ABSTRACT

Method of detecting yarn unevenness appearing as periodic variations of a spun yarn. First, plural yarn samples are taken. Then, k distinct spectrograms are obtained according to the number of the samples. These k spectrums are averaged to create an overall spectrogram. The height of adjacent channels in the overall spectrogram are averaged to create a reference spectrogram. Either the overall spectrogram of the distinct spectrograms are compared with the reference spectrogram of find those portions of the channels that exceed the reference spectrograms in height. These exceeding portions are displayed. Therefore, realistic defective added nonuniformities contained in the spun yarn can be easily detected.

4 Claims, 4 Drawing Sheets

Average Added Unevenness Spectrogram $CH_{AD}$ (L)

Superimposed on Reference Spectrogram $CH_{RF}$

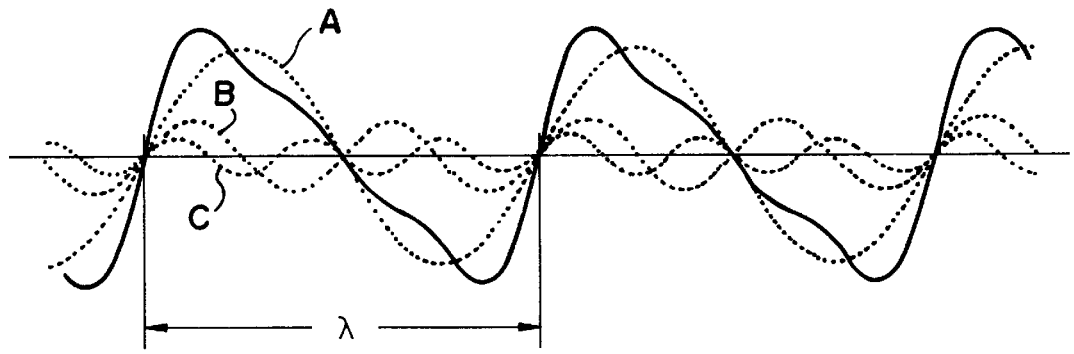
FIG. 1(a) (PRIOR ART)
FIG. 1(b) (PRIOR ART)
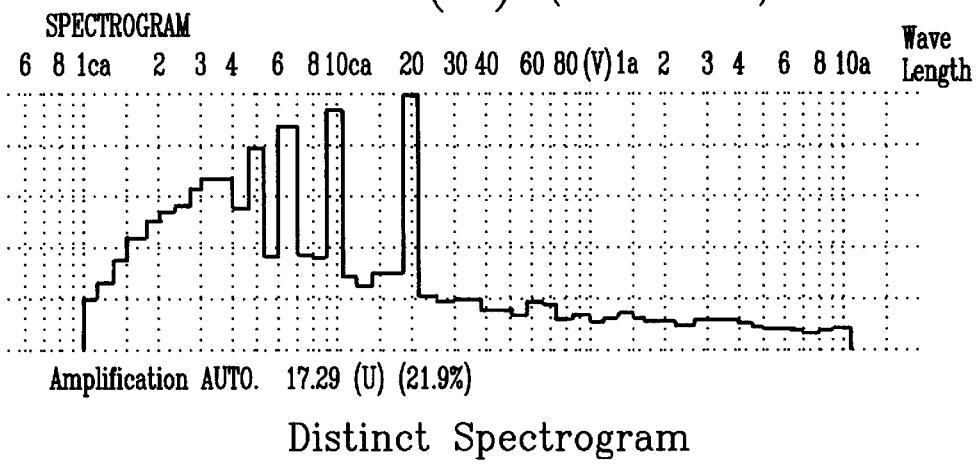
Distinct Spectrogram
FIG. 1(c) (PRIOR ART)
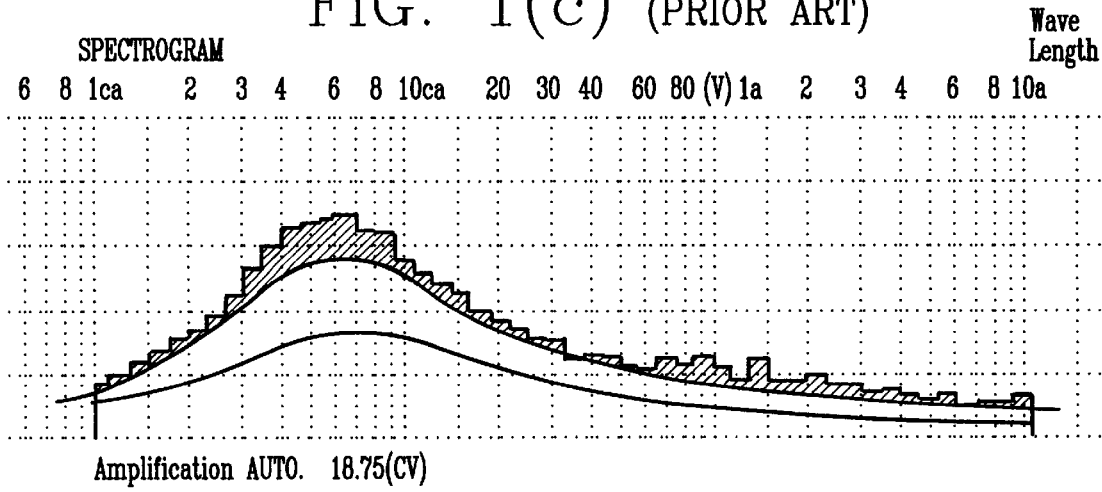
Ideal Spectrum added to Distinct Spectrogram

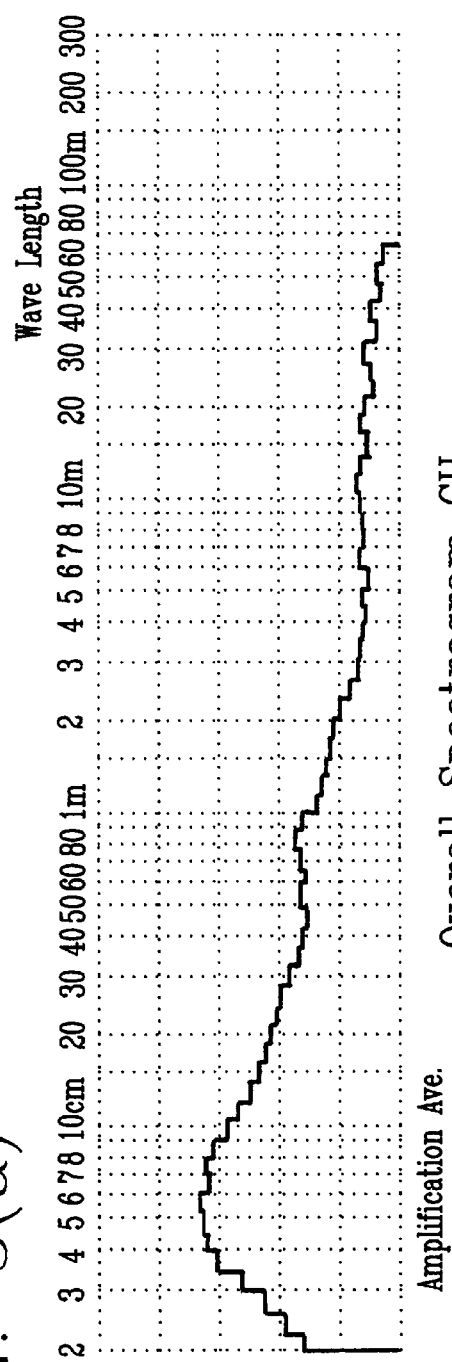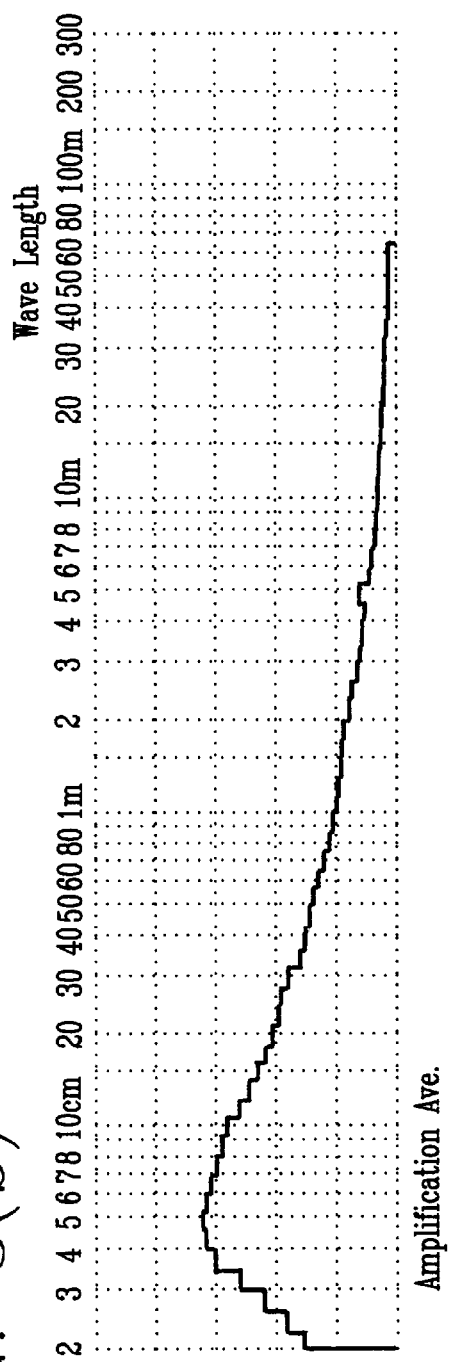

Average Added Unevenness Spectrogram $CH_{AD}$ (L)
Superimposed on Reference Spectrogram $CH_{RF}$ Distinct Added Unevenness Spectrogram

METHOD OF DETECTING YARN UNEVENNESS

FIELD OF THE INVENTION

The present invention relates to a method of detecting unevenness of a spun yarn that appears as periodic variations of the yarn.

BACKGROUND OF THE INVENTION

Generally, in a spinning mill, it is common practice to monitor variations of the thickness of a spun yarn that appear as thicker and thinner portions of the yarn. If a defect is found, the yarn is cut to remove the defect. A testing device is employed for this monitoring operation. This testing device is equipped with measuring capacitors consisting of a pair of electrode plates disposed across a yarn sample passage. If the weight of the traveling yarn sample varies, and if the dielectric constant is thereby changed, the electrical capacitance across the measuring capacitors is varied. The resulting electrical capacitance variation is electronically detected. Thus, the yarn evenness or unevenness is evaluated.

It is known that yarn unevenness including the aforementioned defect is caused by mechanical defects in the spinning process, i.e., improper adjustment or defects in mechanical components. Accordingly, an experienced technician usually has analyzed the circumstances of periodic defects contained in yarn thickness variations represented by the output signal from the testing device to detect the presence or absence of any mechanical defect during a spinning process.

DESCRIPTION OF RELATED ART

A testing device for detecting the unevenness of a spun yarn is sold by Keisokki Kogyo Co., Ltd., Japan, under the product name "Evenness Tester". This tester has a pair of electrodes. A yarn sample is passed across the electrodes, and a signal proportional to a change in the weight of the sample is extracted. In this tester, the dimension of each electrode with respect to the traveling direction of the yarn sample is 8 mm. If the sample is moved at 400 m/min, for example, a length of 2 km of the yarn sample is measured in 5 minutes. If the resultant signal is recorded as a function of time, then a weight diagram is obtained. If the distribution of amplitude is taken, then a weight histogram is derived. Also, as is well known in the art, if CV % and U % are calculated, the rate of variation of the average weight of a sample 8 mm long is obtained.

As shown in FIG. 1(a), periodic variations of the yarn thickness are not limited to perfectly sinusoidal waves. Generally, they contain waveforms distorted greatly out of sinusoidal waves, triangular waves, rectangular waves, and other periodically varying waves. Each of these waves is composed of a fundamental wave having a wavelength of $\lambda$ and higher harmonics waves having submultiple wavelengths such as $\lambda/2$, $\lambda/3$, $\lambda/4$. For example, if the waveform indicated by the solid line in FIG. 1(a) is analyzed, it is observed that a harmonic wave "B" having a wavelength of $\lambda/2$ and a harmonic wave "C" having a wavelength of $\lambda/3$ are contained, as well as a fundamental wave "A" having a wavelength of $\lambda$.

A signal proportional to the weight variation of a yarn sample is taken from it. This signal is decomposed into frequency components or wavelength components by Fourier transform, thus producing a spectrogram as shown in FIG. 1(b). This will hereinafter be referred to as a distinct spectrogram With the aforementioned "Evenness Tester", wavelengths are plotted on the horizontal axis. A wavelength range from one wavelength to its double wavelength is divided into five. Shorter wavelengths are plotted toward the left, while longer wavelengths are plotted toward the right. A logarithmic scale is used in this diagram. More specifically, the wavelength range of a yarn nonuniform component between one wavelength $\lambda_1$ and its double wavelength, i.e., $\lambda_1 \times 2$, is divided into five channels. The height of each channel is taken as the rate of variation of the yarn nonuniform component contained in this channel. Any mechanical defective portion in the spinning step can be detected by analyzing this rate of variation. For example, FIG. 1(b) shows that a rotor incorporated in an openend spinning machine is at fault. A yarn nonuniform component is produced at wavelength 20 cm corresponding to the circumference of the rotor. In addition, channels exhibiting second (wavelength of 10 cm), third (wavelength of 6.7 cm), and fourth (wavelength of 5 cm) harmonic waves protrude. The diagram is so set up that the square root of the total sum of the squares of the values in all the channels is the above-described CV % or U %.

As mentioned previously, a distinct spectrogram indicates the rate of variation of a yarn nonuniform component in one channel. By analyzing this spectrogram, it can be judged whether the machine or components used for the spinning process are at fault.

However, the present situation is that this analysis relies on the experience of a highly experienced technician. In recent years, skilled technicians have decreased in number. Therefore, there is a need for a technique that makes the analysis of the channels as simple as possible.

With respect to this, we, the present inventors, have discovered a novel method. In particular, an ideal rate of variation of substantially uneven spun yarn component is theoretically calculated. This is represented as an ideal spectrum and compared with distinct spectrogram as described above. Thus, those portions of the distinct spectrogram that exceed the ideal spectrum can be clearly and easily found. This ideal spectrum can be theoretically found if the average thickness of the fibers forming the yarn and the distribution of the lengths of the fibers are known. Approximately, instead of this distribution, the average length of the fibers can be used. The average thickness of the fibers can be measured by an instrument sold by Keisokki Kogyo Co., Ltd,, Japan, under product name "Micronaire". Also, the distribution of the lengths of the fibers or the average fiber length can be measured with an instrument sold by Keisokki Kogyo Co., Ltd. under product name "Classifiber".

For example, in FIG. 1(c), the curve of the ideal spectrum is added to distinct spectrogram. Comparison of the distinct spectrogram with the ideal spectrum makes it possible to discriminate those channels clearly exceeding the ideal spectrum. Hence, any periodic defect of the sample can be easily discerned.

As shown in FIG. 1(c), distinct spectrogram obtained from actual yarn samples are always higher than the ideal spectrum in every channel. This is referred to as the "I index", which is produced by the existence of any uneven component added by the influence of movement of the machine used for the spinning process. The "I index" becomes higher as more defects exist in the adjustment of the machine or in the components. In the spinning process, if a defect or the above-described added uneven component is present in its initial stage, the component is lengthened in the final stage, resulting in a defect or nonuniformity of a long wavelength. Therefore, one can judge which of the spinning steps is problematic by reading the wavelength and height of the added uneven component in each distinct spectrogram. Specifically, of those portions of the distinct spectrogram, channels within the range of the "I index" can be judged to be free of problems. However, if any channel is much higher than its adjacent channels, e.g., higher by a factor of 1.5 or more, it follows that any periodic uneven component exceeds the allowable "I index" range. Consequently, one should determine that a mechanical defect having a period corresponding to the higher channel is present.

In this method that relies on comparison of the ideal spectrum with distinct spectrogram, the decision to see whether the represented heights of the channels are due to any defect of the yarn during the spinning process is made further based on experience. As described above, distinct spectrogram obtained from a yarn sample is displayed as having heights exceeding the ideal spectrum throughout the channels. Hence, some portions of the distinct spectrogram should be judged to be free from defects, i.e., to lie within the allowable "I index" range. Also, yarns supplied to the market have various grades and other various factors. For example, with respect to yarns designed to provide high quality, the "I index" must be strictly judged. On the other hand, with respect to yarns designed to provide low quality, the "I index" should be judged less strictly. In consequence, the decision is difficult to make.

SUMMARY OF THE INVENTION

It is an object of the present invention to provide a method of detecting uneven yarn components of a yarn of interest in such a way that added uneven components which are not required to be regarded as defective can be judged not to be due to any defect, and that any important added uneven component which should be regarded as defective can be found at a glance.

One aspect of the present invention lies in a method of detecting uneven yarn components, the method comprising the steps of: taking plural samples from a yarn to be investigated; moving the samples; extracting signals proportional to variations of weights of the samples; analyzing the signals in terms of frequency or wavelength to produce signal components of different wavelengths indicative of any uneven yarn component; classifying the signal components into plural channels; and creating distinct spectrograms representing the rates of variation of the signal components in terms of height of channel. This method is characterized by the following procedure. Let k be the number of the distinct spectrograms obtained according to the number of the samples. These spectrograms are averaged to create an overall spectrogram. The heights of channels adjacent to each other in the overall spectrogram are averaged to form a reference spectrogram. Then, this reference spectrogram is compared with the overall spectrogram. The heights of some portions of some channels of the overall spectrogram may exceed the reference spectrogram. These exceeding portions are displayed. In this way, any defective yarn nonuniformity is detected.

In a second aspect of the invention, a reference spectrogram is created in the same way as in the first aspect. Distinct spectrograms are compared with the reference spectrogram. The heights of some portions of some channels of the distinct spectrograms may exceed the reference spectrogram. These exceeding portions are displayed. Thus, any defective yarn nonuniformity is detected.

In a third aspect, the exceeding portions of the exceeding channels are displayed in different colors either on a display device or on paper according to the amounts of excess.

Other objects and features of the invention will appear in the course of the description thereof, which follows.

BRIEF DESCRIPTION OF DRAWINGS

FIG. 1(a) is a waveform diagram of a signal obtained from variations of the weight of a yarn by the prior art method, showing periodically varying uneven components of the yarn and plural wavelength components of yarn unevenness;

FIG. 1(b) is a distinct spectrogram giving one example of spectrogram obtained by Fourier-transforming a signal obtained from variations of the weight of a yarn by the prior art techniques;

FIG. 1(c) is a spectrogram similar to FIG. 1(b), but in which the curve of an ideal spectrogram is added in accordance with the present invention;

FIG. 3(a) is an overall spectrogram created from k distinct spectrograms in accordance with the invention;

FIG. 3(b) is a reference spectrogram created from an overall spectrogram in accordance with the invention;

DESCRIPTION OF PREFERRED EMBODIMENTS

The preferred embodiments of the present invention are hereinafter described by referring to the accompanying drawings.

Figure 2A:
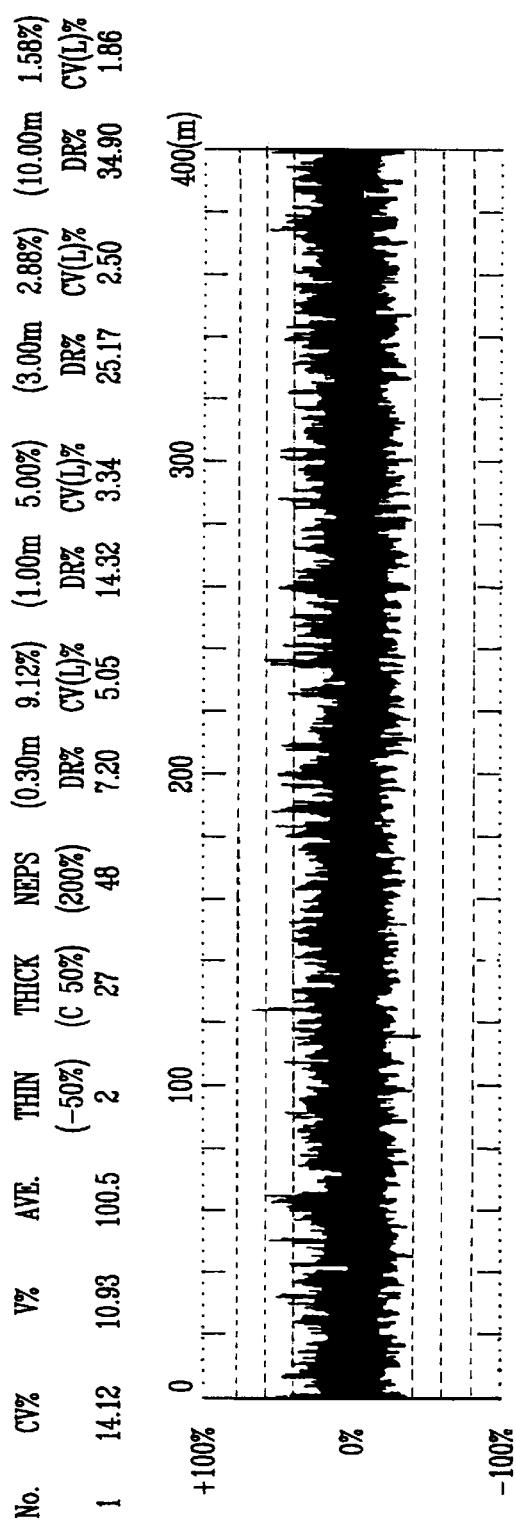
FIG. 2(a) is a waveform diagram of an analog signal proportional to variations of the weight of a yarn sample in motion where the unevenness of the yarn is being measured by the prior art method.
Figure 2B:
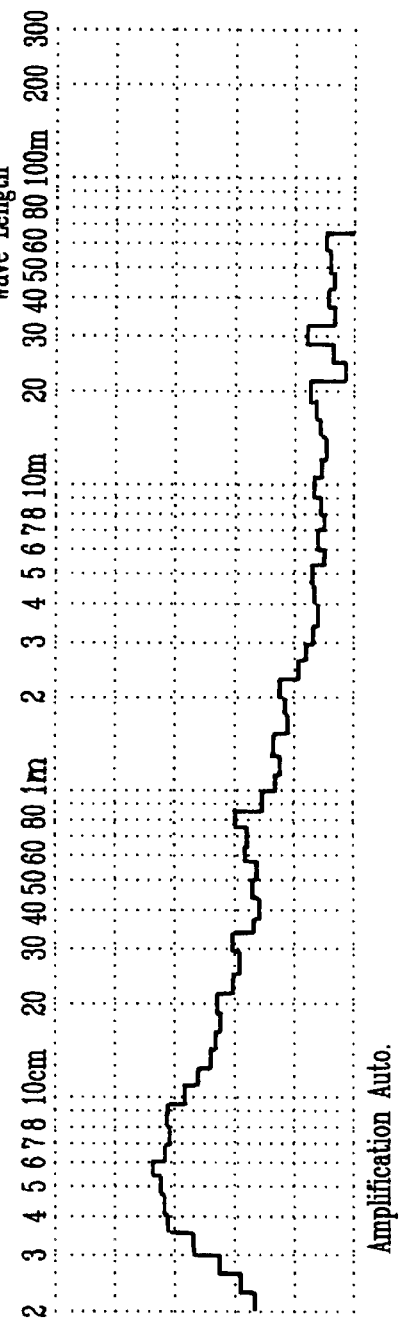
FIG. 2(b) is a distinct spectrogram obtained by frequency-analyzing a signal proportional to variations of the weight of a yarn sample in motion where the unevenness of the yarn is being measured by the prior art method.

First, plural yarn samples are taken from a yarn to be investigated. Each sample is passed across a pair of electrodes. A signal proportional to the variation of the weight of each sample is taken. Then, the signals are analyzed in terms of frequency or wavelength to extract uneven yarn components of various wavelengths. These components are classified into several channels. The rate of variation of each uneven yarn component is represented by the height of the corresponding channel. Thus, distinct spectrograms are created. This method is similar to the above-described prior art method up to this point. FIG. 2(a) shows the waveform of an analog signal recorded by the "Evenness Tester" described above. FIG. 2(b) shows distinct spectrograms recorded by the "Evenness Tester".

Accordingly, k distinct spectrograms $CH_n$ are obtained from plural yarn samples (e.g., at least five, normally 10, more than 20 in some cases).

To review a problem common to all the samples, the k distinct spectrograms $CH_n$ (n=1, 2, . . . , k) are averaged to create an overall spectrogram $CH_{OA}$ as shown in FIG. 3(a). More specifically, this overall spectrogram $CH_{OA}$ is calculated from the k distinct spectrograms $CH_n$ for each of the channels L according to the following Equation (1). The results for all the channels are combined into one diagram, thus giving the overall spectrogram $CH_{OA}$.

$$CH_{OA(L)} = \sqrt{\sum_{n=1}^{k} \frac{\{CH_{n(L)}\}^2}{k}} \qquad (1)$$

Subsequently, a reference spectrogram $CH_{RF}$ as shown in FIG. 3(b) is created from the overall spectrogram $CH_{OA}$ according to the following (1) to (4).

(1) If any channel $CH_{OA(L)}$ of the overall spectrogram is higher than its adjacent channels, the height is corrected to the average value of these adjacent channels. That is, the height of the corrected channel is made equal to the average value of the heights of its adjacent channels. It is to be noted, however, the leftmost channel is compared only with its adjacent right channel. The rightmost channel is compared only with its adjacent left channel. Their heights are corrected to these calculated average values. This correcting processing is carried out from the leftmost channel (exhibiting the shortest wavelength) of the overall spectrogram to the right channel. As a result, a channel exhibiting a peak height (in the illustrated example, the channel at a wavelength of 5 cm) is formed. The channels located on the right side of this highest channel have monotonously decreasing heights. Theoretically, the peak wavelength is 2.5 to 3 times as long as the average fiber length LF of the samples. Therefore, the above-described correction to the average value may be performed up to a right channel showing a wavelength of more than 4×LF.

(2) Accordingly, it is assumed that the channels decrease in height in geometric series from the highest channel to the described in item (1) to the right channel. Its common ratio is calculated.

(3) With respect to channels showing wavelengths longer than 4×LF, their heights are corrected to values computed by using the common ratio described in item (2) above.

(4) Then, the individual channels $CH_{OA(L)}$ of the overall spectrogram that have been corrected in this way are combined to create a reference spectrogram $CH_{RF}$.

Therefore, this reference spectrogram $CH_{RF}$ is closer to an ideal spectrum as shown in FIG. 1(c) than the overall spectrogram $CH_{OA}$. Notice that the ideal spectrum is theoretically completely ideal but the reference spectrogram $CH_{RF}$ is a realistic target spectrogram that is obtained by removing only periodic defects from the overall spectrogram $CH_{OA}$, which in turn is obtained from plural measured samples.

Consequently, it is possible to judge whether the measured samples contain any realistic unneglected periodic defect, by comparing either the overall spectrogram $CH_{OA}$ or the distinct spectrograms $CH_n$ with the reference spectrogram $CH_{RF}$ to find those portions having heights exceeding the reference spectrogram $CH_{RF(L)}$ for each channel. That is, if these portions are present, they can be judged to contain any periodic defect or defective added nonuniformity.

First Embodiment

In the first embodiment of the present invention, the reference spectrogram $CH_{RF}$ is compared with the overall spectrogram $CH_{OA}$. For each channel L, an average added unevenness spectrogram $CH_{AD(L)}$ is calculated according to Equation (2) below. The results for each channel are combined as shown in FIG. 4(a).

$$\sqrt{\{CH_{OA(L)}\}^2 - \{CH_{RF(L)}\}^2} = CH_{AD(L)} \qquad (2)$$

Figure 4A:
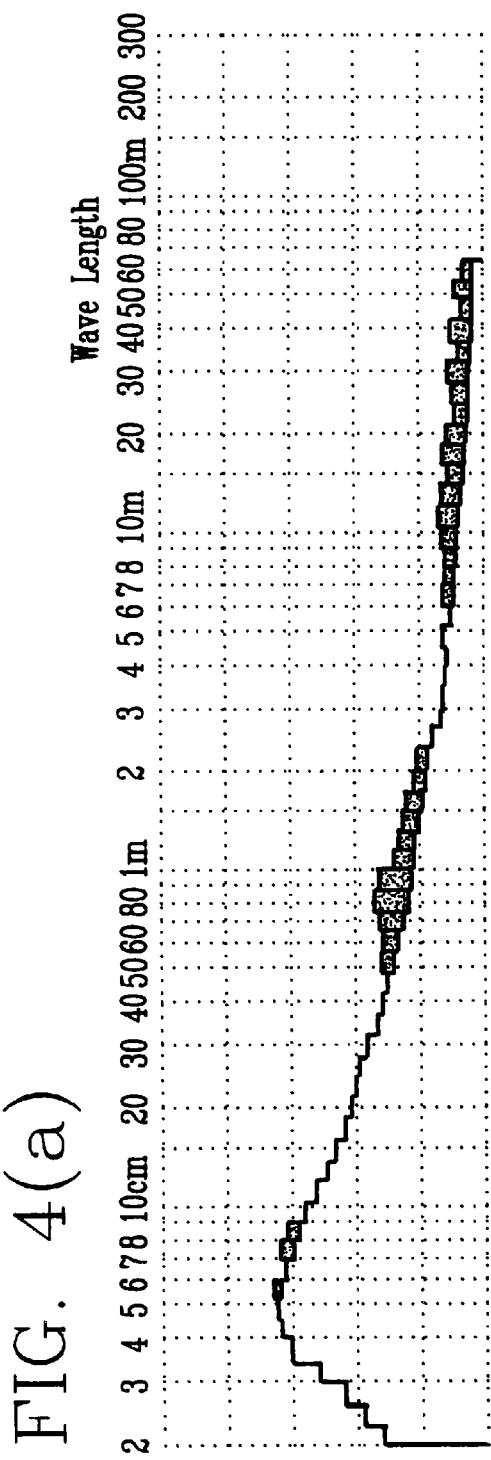
FIG. 4(a) is a spectrogram of a defective added uneven component displayed in accordance with the invention, and in which an average added unevenness spectrogram is superimposed on a reference spectrogram.

In FIG. 4(a), the average added unevenness spectrogram $CH_{AD(L)}$ is shown to be superimposed on the reference spectrogram $CH_{RF}$. It is also possible to extract only portions of those average added unevenness spectrograms $CH_{AD(L)}$ that exceed the reference spectrogram $CH_{RF}$ and to display them.

Second Embodiment

In the second embodiment of the present invention, distinct spectrograms $CH_n$ (n=1, 2, . . . , k) are compared with the reference spectrogram $CH_{RF}$. A distinct added unevenness spectrogram $CH_{nAD(L)}$ is calculated for each channel L according to the following Equation (3), The results are combined and displayed as k distinct added unevenness spectrograms $CH_{1AD}, CH_{2AD}, \ldots CH_{kAD}$, as shown in FIG. 4(b).

$$\sqrt{\{CH_{n(L)}\}^2 - \{CH_{RF(L)}\}^2} = CH_{nAD(L)} \qquad (3)$$

Figure 4B:
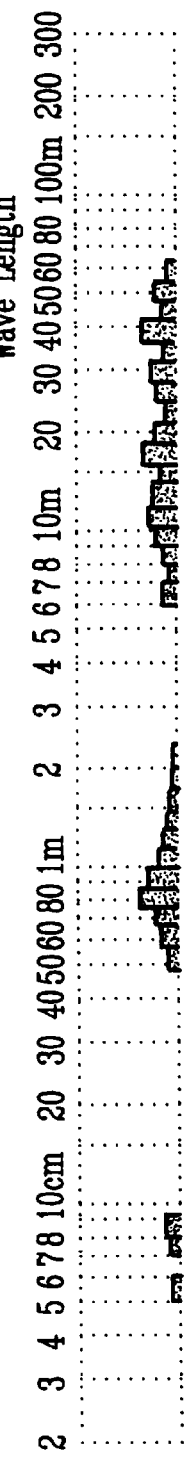
FIG. 4(b) is another spectrogram of a defective added uneven component displayed in accordance with the invention, and in which distinct added unevenness spectrograms are displayed alone.

In FIG. 4(b), each of the k distinct added unevenness spectrograms $CH_{1AD}, CH_{2AD}, \ldots, CH_{kAD}$ is shown alone. These spectrograms may be superimposed on the reference spectrogram $CH_{RF}$.

The above-described average added unevenness spectrograms $CH_{AD(L)}$ and/or distinct added unevenness spectrograms $CH_{kAD}$ are displayed on a computer display or printed on paper by a printer. Preferably, exceeding portions of exceeding channels are displayed in different colors according to the amounts of excess. For instance, if the value of $CH_{AD(L)}$ calculated according to Equation (2) or the value of $CH_{n(L)}$ computed according to Equation (3) is 5 or more, the exceeding portions of the spectrogram is colored gray. If the value is between 4 and 5, the exceeding portions of the spectrogram is colored red. If the value is between 3 and 4, the exceeding portions of the spectrogram is colored yellow. If the value is between 2 and 3, the exceeding portions of the spectrogram is colored blue. If the value is between 1 and 2, the exceeding portions of the spectrogram is colored white. In this way, various values can be displayed in different colors. Thus, any defective added unevenness can be displayed clearly.

Where the average added unevenness spectrogram $CH_{AD(L)}$ is shown to be superimposed on the reference spectrogram as shown in FIG. 4(a), or where the k distinct added unevenness spectrograms $CH_{1AD}, CH_{2AD}, \ldots, CH_{kAD}$ are shown to be superimposed on the reference spectrogram, the ideal spectrum may be displayed at the same time.

Effects of the Invention

In the present invention, k distinct added unevenness spectrograms $CH_n$ are obtained according to the number of yarn samples, and these are averaged to create an overall spectrogram $CH_{OA}$. Also, the average values of the heights of the channels adjacent to each channel of the overall spectrogram $CH_{OA}$ are calculated to create a reference spectrogram $CH_{RF}$. Either the overall spectrogram $CH_{OA}$ or the distinct spectrograms $CH_n$ are compared with the reference spectrogram $CH_{RF}$. Those average added unevenness spectrograms $CH_{AD(L)}$ or distinct added unevenness spectrograms $CH_{kAD}$ that exceed the reference spectrogram $CH_{RF}$ are displayed for each channel. Therefore, any defective added unevenness can be judged at a glance.

This is described in further detail As shown in FIG. 1(c), where any added unevenness is detected, based on a theoretically found ideal spectrum, every added nonuniformity within the range of the permitted "I index" is displayed. Therefore, it is difficult to detect any realistic defect of the yarn of interest. In contrast, in the present invention, the average value of k distinct added unevenness spectrograms $CH_n$ is calculated to derive an overall spectrogram $CH_{OA}$. A reference spectrogram $CH_{RF}$ is created from this overall spectrogram $CH_{OA}$. Any added nonuniformity is detected, using the reference spectrogram $CH_{RF}$ as a reference. Hence, only realistic defective added nonuniformities can be easily detected by removing permitted added nonuniformities. In this way, this method offers great advantages.

If exceeding portions of exceeding channels of the above-described average added unevenness spectrograms $CH_{AD(L)}$ or distinct added unevenness spectrograms $CH_{kAD}$ are displayed on a computer display or printed on paper in different colors according to the amounts of excess, any defective added unevenness of interest can be checked visually more easily.

What is claimed is:

1. A method of detecting uneven yarn components by taking plural samples from a yarn to be investigated, moving the samples, extracting signals proportional to variations of weights of the samples, analyzing the signals in terms of frequency or wavelength to produce signal components of different wavelengths indicative of any uneven yarn component, classifying the signal components into plural channels, and creating distinct spectrograms representing rates of variation of the signal components in terms of height of channel, said method comprising the steps:

obtaining k distinct spectrograms $CH_n$ (n=1, 2, ..., k) according to the number of said yarn samples;

averaging said k distinct spectrograms with respect to each signal component in each channel thereof to create an overall spectrogram $CH_{OA}$ as one diagram which may contain defective unevenness common to all the samples;

averaging said overall spectrogram $CH_{OA}$ in a manner averaging heights between adjacent channels thereof to create a realistic reference spectrogram $CH_{RF}$ in which periodic defects have been removed from said overall spectrogram $CH_{OA}$;

comparing said reference spectrogram $CH_{RF}$ and said overall spectrogram $CH_{OA}$ to find exceeding portions of the channels in the overall spectrogram $CH_{OA}$, said exceeding portions exceeding said reference spectrogram $CH_{RF}$ in height; and displaying these exceeding portions as an average added unevenness spectrogram $CH_{AD}$.

2. The method of claim 1, wherein said exceeding portions of said exceeding channels are displayed in colors differentiated according to its amount of excess.

3. A method of detecting uneven yarn components by taking plural samples from a yarn to be investigated, moving the samples, extracting signals proportional to variations of weights of the samples, analyzing the signals in terms of frequency or wavelengths to produce signal components of different wavelengths indicative of any uneven yarn component, classifying the signal components into plural channels, and creating distinct spectrograms representing rates of variation of the signal components in terms of height of channel, said method comprising the steps:

obtaining k distinct spectrograms $CH_n$ (n=1, 2, ..., k) according to the number of said yarn samples;

averaging said k distinct spectrograms with respect to each signal component in each channel thereof to create an overall spectrogram $CH_{OA}$ as one diagram which may contain defective unevenness common to all the samples;

averaging said overall spectrogram $CH_{OA}$ in a manner averaging heights between adjacent channels thereof to create a realistic reference spectrogram $CH_{RF}$ by removing periodic defects from said overall spectrogram $CH_{OA}$;

comparing said distinct spectrograms $Ch_n$ and said reference spectrogram $CH_{RF}$ to find exceeding portions of the channels in the distinct spectrograms, said exceeding portions exceeding said reference spectrogram $CH_{RF}$ in height; and displaying these exceeding portions as an average added unevenness spectrogram $CH_{AD}$.

4. The method of claim 3, wherein said exceeding portions of said exceeding channels are displayed in colors differentiated according to its amount of excess.

* * * * *